United States Patent [19]

Backer et al.

[11] Patent Number: 5,461,029
[45] Date of Patent: Oct. 24, 1995

[54] METHOD OF TREATING HERPES VIRAL INFECTIONS USING HBNF AND MK PROTEINS

[75] Inventors: Joseph M. Backer, Tenafly; Michael R. Ostrander, Glen Ridge, both of N.J.

[73] Assignee: American Cyanamid Company, Wayne, N.J.

[21] Appl. No.: 874,848

[22] Filed: Apr. 24, 1992

[51] Int. Cl.$^6$ ............... A61K 38/16; A61K 38/18
[52] U.S. Cl. ............... 514/2; 530/350; 514/934; 424/229.1; 424/230.1; 424/231.1
[58] Field of Search ............... 514/2, 8, 934; 530/350, 395; 435/69.1

[56] References Cited

U.S. PATENT DOCUMENTS 5,210,026  5/1993  Kovesdi et al. ............... 435/69.1

FOREIGN PATENT DOCUMENTS

| | | |
|---|---|---|
| 0275204A2 | 7/1988 | European Pat. Off. . |
| 0281822A2 | 9/1988 | European Pat. Off. . |
| 0320148A1 | 6/1989 | European Pat. Off. . |
| WO89/00198 | 1/1989 | WIPO . |

OTHER PUBLICATIONS

Tomomura, M., et al. (1990) Biochem. Biophys. Res. Comm. 171:603–609.
Raurala, H. (1989) EMBO J. 8: 2933–2941.
WuDunn, D., et al. (1989) J. Virol. 63:52–58.
Kovesdi, I. et al. (1990) Biochem. Biophys. Res. Comm. 172: 850–854.
Kretschmer, P. J., et al. (1991) Growth Factors 5: 99–114.
Hirsch, M. S. et al. (1987) Scientific American 256(4): 66–75.
Kaner, R. J., et al. (1990) Science 248: 1410–1413.
Receptor–and heparin–binding domains of basic fibroblast growth factor, P.N.A.S. vol. 85: 2324–2328 (Apr. 1988).
Carboxyl–terminal structure of basic fibroblast growth factor significantly contributes to its affinity for heparin, Eur. J. Bioch., vol. 188: 239–245 (1990) Seno, M. et al.

*Primary Examiner*—Garnette D. Draper
*Assistant Examiner*—David L. Fitzgerald

[57] ABSTRACT

The disclosure relates to a method of inhibiting the infectivity of a virus, the virus being characterized by the presence of a heparin-binding protein, which comprises contacting the cellular receptor for the virus or the receptor-binding protein of the virus with an effective amount of a pharmaceutical composition containing the HBNF protein, the MK protein or a combination thereof in a sufficient amount to inhibit the infectivity of the virus. Also, this disclosure concerns a method of preventing or treating a viral infection in a subject, the virus being characterized by the presence of a heparin-binding protein, which comprises administering to the subject an effective amount of a pharmaceutical composition containing HBNF, MK or a combination thereof in a sufficient amount to prevent or treat the viral infection in the subject. Further, the disclosure describes a new composition comprising a combination of the HBNF and MK proteins. Both HBNF and MK possess heparin-binding activity, displace bFGF from high affinity receptors and inhibit growth of endothelial cells.

7 Claims, 6 Drawing Sheets

```
  1 CGGGCCAAGCAGCGCGGGCAGCGAG

26 ATG CAG CAC CGA GGC TTC CTC CTC CTC ACC CTC CTC GCC CTG CTG GCG CTC ACC
-22  M   Q   H   R   G   F   L   L   L   T   L   L   A   L   L   A   L   T

80 TCC GCG GTC GCC AAA AAG AAA GAT AAG GTG AAG AAG GGC GGC CCG GGG AGC GAG
 -4  S   A   V   A   K   K   K   D   K   V   K   K   G   G   P   G   S   E

134 TGC GCT GAG TGG GCC TGG GGG CCC TGC ACC CCC AGC AGC AAG GAT TGC GGC GTG
 15  C   A   E   W   A   W   G   P   C   T   P   S   S   K   D   C   G   V

188 GGT TTC CGC GAG GGC ACC TGC GGG GCC CAG ACC CAG CGC ATC CGG TGC AGG GTG
 33  G   F   R   E   G   T   C   G   A   Q   T   Q   R   I   R   C   R   V

242 CCC TGC AAC TGG AAG AAG GAG TTT GGA GCC GAC TGC AAG TAC AAG TTT GAG AAC
 51  P   C   N   W   K   K   E   F   G   A   D   C   K   Y   K   F   E   N

296 TGG GGT GCG TGT GAT GGG GGC ACA GGC ACC AAA GTC CGC CAA GGC ACC CTG AAG
 69  W   G   A   C   D   G   G   T   G   T   K   V   R   Q   G   T   L   K

350 AAG GCG CGC TAC AAT GCT CAG TGC CAG GAG ACC ATC CGC GTC ACC AAG CCC TGC
 87  K   A   R   Y   N   A   Q   C   Q   E   T   I   R   V   T   K   P   C

404 ACC CCC AAG ACC AAA GCA AAG GCC AAA GCC AAG AAA GGG AAG GGA AAG GAC TAG
105  T   P   K   T   K   A   K   A   K   A   K   K   G   K   G   K   D   *

458 ACGCCAAGCCTGGATGCCAAGGAGCCCCTGGTGTCACATGGGGCCTGGCCACGCCCTCCCTCTCCCAGGC
528 CCGAGATGTGACCCACCAGTGCCTTCTGTCTGCTCGTTAGCTTTAATCAATCATGCCCTGCCTTGTCCCT
598 CTCACTCCCCAGCCCCACCCCTAAGTGCCCAAAGTGGGGAGGGACAAGGGATTCTGGGAAGCTTGAGCCT
568 CCCCCAAAGCAATGTGAGTCCCAGAGCCCGCTTTTGTTCTTCCCCACAATTCCATTACTAAGAAACACAT
738 CAAATAAACTGACTTTTTCCCCCCAATAAAAGCTCTTCTTTTTTAATATAAAAAAAAAAAAAA
```

FIG.1

Gly-Lys-Lys-Glu-Lys-Pro-Glu-Lys-Lys-Val-Lys-Lys-Ser-Asp-Cys-Gly-Glu-Trp-Gln-Trp-
Ser-Val-Cys-Val-Pro-Thr-Ser-Gly-Asp-Cys-Gly-Leu-Gly-Thr-Arg-Glu-Gly-Thr-Arg-Thr-
Gly-Ala-Glu-Cys-Lys-Gln-Thr-Met-Lys-Thr-Gln-Arg-Cys-Lys-Ile-Pro-Cys-Asn-Trp-Lys-
Lys-Gln-Phe-Gly-Ala-Glu-Cys-Lys-Tyr-Gln-Phe-Gln-Ala-Trp-Gly-Glu-Cys-Asp-Leu-Asn-
Thr-Ala-Leu-Lys-Thr-Arg-Thr-Gly-Ser-Leu-Lys-Arg-Ala-Leu-His-Asn-Ala-Asp-Cys-Gln-
Lys-Thr-Val-Thr-Ile-Ser-Lys-Pro-Cys-Gly-Lys-Leu-Thr-Lys-

FIG.2

```
   1  AAGTAAATAAACTTTAAAAAATGGCCTGAGTTAAGTGTATTAAAAAGAAGAAATAGTCGTAAGATGGCAGT
  71  ATAAATTCATCTCTGCTTTTAATAAGCTTCCCAATCAGCTCTCGAGTGCAAAGCGCTCTCCCTCCCTCGC
 141  CCAGCCTTCGTCCTCCTGGCCCGCTCCTCTCATCCCTCCCATTCTCCATTTCCCTTCCGTTCCCTCCCTG
 211  TCAGGGCGTAATTGAGTCAAAGGCAGGATCAGGTTCCCCGCCTTCCAGTCCAAAAATCCCGCCAAGAGAG
 281  CCCCAGAGCAGAGGAAAATCCAAAGTGGAGAGAGGGGAAGAAAGAGACCAGTGAGTCATCCGTCCAGAAG
 351  GCGGGGAGAGCAGCAGCGGCCCAAGCAGGAGCTGCAGCGAGCCGGGTACCTGGACTCAGCGGTAGCAACC
 421  TCGCCCCTTGCAACAAAGGCAGACTGAGCGCCAGAGAGGACGTTTCCAACTCAAAA
```

```
 477  ATG CAG GCT CAA CAG TAC CAG CAG CAG CGT CGA AAA TTT GCA GCT GCC TTC TTG
 -32   M   Q   A   Q   Q   Y   Q   Q   Q   R   R   K   F   A   A   A   F   L

531  GCA TTC ATT TTC ATA CTG GCA GCT GTG GAT ACT GCT GAA GCA|GGG AAG AAA GAG
 -14   A   F   I   F   I   L   A   A   V   D   T   A   E   A | G   K   K   E

585  AAA CCA GAA AAA AAA GTG AAG AAG TCT GAC TGT GGA GAA TGG CAG TGG AGT GTG
   5   K   P   E   K   K   V   K   K   S   D   C   G   E   W   Q   W   S   V

639  TGT GTG CCC ACC AGT GGA GAC TGT GGG CTG GGC ACA CGG GAG GGC ACT CGG ACT
  23   C   V   P   T   S   G   D   C   G   L   G   T   R   E   G   T   R   T

639  GGA GCT GAG TGC AAG CAA ACC ATG AAG ACC CAG AGA TGT AAG ATC CCC TGC AAC
  41   G   A   E   C   K   Q   T   M   K   T   Q   R   C   K   I   P   C   N

747  TGG AAG AAG CAA TTT GGC GCG GAG TGC AAA TAC CAG TTC CAG GCC TGG GGA GAA
  59   W   K   K   Q   F   G   A   E   C   K   Y   Q   F   Q   A   W   G   E

801  TGT GAC CTG AAC ACA GCC CTG AAG ACC AGA ACT GGA AGT CTG AAG CGA GCC CTG
  77   C   D   L   N   T   A   L   K   T   R   T   G   S   L   K   R   A   L

855  CAC AAT GCC GAA TGC CAG AAG ACT GTC ACC ATC TCC AAG CCC TGT GGC AAA CTG
  95   H   N   A   E   C   Q   K   T   V   T   I   S   K   P   C   G   K   L

909  ACC AAG CCC AAA CCT CAA |GCA|GAA TCT AAG AAG AAG AAA AAG GAA GGC AAG AAA
 113   T   K   P   K   P   Q  | A | E   S   K   K   K   K   K   E   G   K   K

963  CAG GAG AAG ATG CTG GAT TAA
 131   Q   E   K   M   L   D   *
```

```
 984  AAGATGTCACCTGTGGAACATAAAAAGGACATCAGCAAACAGGATCAGTTAACTATTGCATTTATATGTA
1054  CCGTAGGCTTTGTATTCAAAAATTATCTATAGCTAAGTACACAATAAGCAAAAACAACCAATTTGGGTTC
1124  TGCAGGTACATAGAAGTTGCCAGCTTTTCTTGCCATCCTCGCCATTCGAATTTCAGTTCTGTACATCTGC
1194  CTATATTCCTTGTGATAGTGCTTTGCTTTTTTCATAGATAAGCTTCCTCCTTGCCTTTCGAAGCATCTTTT
1264  GGGCAAACTTCTTTCTCAGGCGCTTGATCTTCAGCTCTGCGAAATTCCTTCGCTTTTTCTTAAGGGTTTC
1334  TGGCACAGCAGGAACCTCCTTCTTCTTCTCTTCTACACCCTCTATGTACC
```

FIG.3B

METHOD OF TREATING HERPES VIRAL INFECTIONS USING HBNF AND MK PROTEINS

Throughout this application, various references are referred to by arabic numerals in parentheses to more fully describe the state of the art to which this invention pertains. A full bibliographic citation for each reference is provided at the end of the specification, immediately preceding the sequence listing. The disclosures of these references are hereby incorporated by reference into this application.

BACKGROUND OF THE INVENTION

The Herpesviridae are common infectious agents. For example, the herpes simplex viruses (HSV) are infectious agents which cause a number of diseases. The entry of HSV in the target cells begins with binding of the virus to the cell surface heparan sulfate proteoglycans (1, 2). Several experimental lines of evidence prove the existence and importance of this binding. First, in HEp-2 cells, enzymatic digestion of cell surface heparan sulfate proteoglycans (HSP) with heparitinase and heparinase decreases binding of HSV-1 and HSV-2 to the cells, as well as plaque formation (1). Second, heparin, heparan sulfate, cationic aminoglycosides, poly-L-lysine and heparin-binding protein PF4 decrease binding and infectivity of HSV in several experimental systems (1–8). All these compounds can inhibit virus association with the cell surface either by binding to the cellular HSP, or by binding to the viral proteins capable of interaction with HSP. Third, purified HSV and its glycoproteins gB and gC bind to heparin-Sepharose beads (9). The gB is an "indispensable" envelope glycoprotein which is involved in penetration of virus into target cell, while gC, although a "dispensable" glycoprotein, plays an important role in both absorption and penetration of virus (10–14). A similar role is played by the gB and gC homologs in another member of herpes family: human cytomegalovirus (15,16). Recently, it was suggested that HSV can utilize a high-affinity receptor for a heparin-binding growth factor bFGF, as a "portal for cellular entry" (17, 18). However, subsequent studies indicated that high affinity bFGF receptor is not necessarily involved in HSV binding (19–21). These contradictory results may be reconciled by the discovery that interaction of bFGF with cell surface HSP or soluble heparin is a necessary step in the process of bFGF binding to high affinity receptor (22–24). The latter findings may explain why under certain experimental conditions, bFGF may inhibit viral adsorption and infectivity without direct involvement of bFGF high affinity receptor.

SUMMARY OF THE INVENTION

This invention provides a pharmaceutical composition useful for inhibiting the infectivity of a virus, the composition comprising an effective viral inhibiting amount of HBNF, MK, or a combination of both, and a pharmaceutically acceptable carrier. Also provided is a method of inhibiting the infectivity of a virus by contacting the virus with the pharmaceutical compositions of this invention. Methods of treating or preventing a viral infection are further provided. These methods comprise administering to a subject an effective amount of HBNF, MK, or a combination of both and a pharmaceuticaly acceptable carrier.

BRIEF DESCRIPTION OF THE FIGURES

FIG. 1 (See also SEQ ID NO: 1). Nucleotide and amino acid sequence of the human MK gene. Bold-faced amino acids represent the predicted protein presequence, the arrow represents the predicted N-terminus of the mature protein, and the two peptide sequences corresponding to primers 1 and 2 used to amplify the mouse genomic DNA probe are underlined. The two polyadenylation sequences near the 3' end of the gene are underlined.

FIG. 2 shows a partial, 114 amino acid sequence of bovine HBNF.

FIGS. 3A and 3B (See also SEQ ID NO: 4). Complementary DNA cloning, nucleotide and deduced amino acid sequence of human HBNF. FIG. 3A Diagram of four overlapping partial cDNAs encoding HBNF. Top line indicates the mRNA with black and hatched boxes representing the HBNF coding region and postulated 3'poly(A) tract respectively. Restriction sites: H=HindIII, K=Kpn1, P=Pst1, nt=nucleotide length of clones. FIG. 3B. Combined nucleotide sequence of clones HHC7, 8, 10 and 12 with deduced amino acid sequence (single-letter code). Amino acids shown in normal type indicate the 136 amino acids of mature human HBNF preceded by an additional 32 bold-faced amino acids representing a potential 168 amino acid precursor protein.

DETAILED DESCRIPTION OF THE INVENTION

Figure 3A:
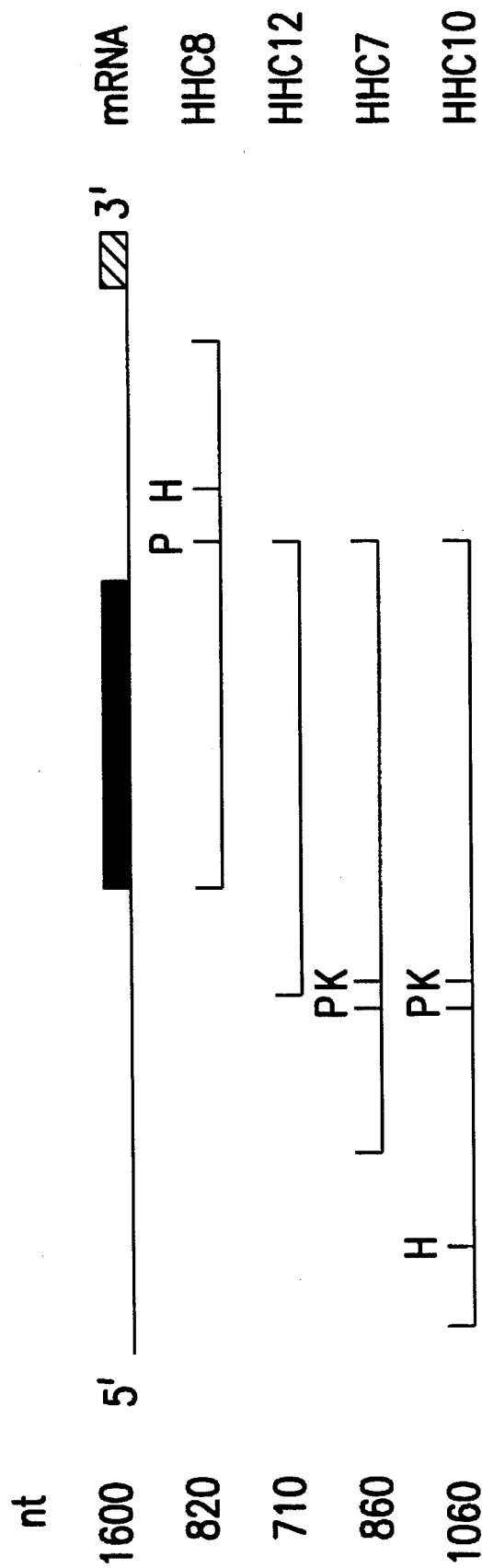

Two novel heparin-binding proteins, referred to as HBNF and MK (see, 25, for review), displace bFGF from high affinity receptors and inhibit growth of endothelial cells (26). These activities of HBNF and MK are observed at submicromolar concentrations and, apparently, mediated by cell surface HSPs. Both proteins inhibit infectivity of Herpesviridae virus, e.g., HSV type 1 and 2 as measured in plaque reduction assay. This effect is due to the inhibition of viral adsorption to the cell surface. Similar results were obtained with HCMV. Thus, heparin-binding proteins are antiviral drugs which can block infection, thereby limiting the spread of virus infection and reinfection in the lesions.

This invention provides a pharmaceutical composition useful for inhibiting the infectivity of a virus, the virus being characterized by the presence of a heparin-binding protein, comprising an effective amount of HBNF or MK, alone or in combination, and a pharmaceutically acceptable carrier. Alternatively, these pharmaceutical compositions also may comprise other antiviral compounds. Examples of such compounds include, but are not limited to, acyclovir (Zovirax™, Burroughs Wellcome Company), ganciclovir (Cytovene™, Syntex Laboratories, Inc.), foscarnet (Foscavir™, Astra), vidarabine (Vira-A™, Parke Davis) and trifluriodine (Viroptic™, Burroughs Wellcome Company).

In the preferred embodiment of this invention, the virus is a Herpseviridae virus, e.g., herpes simplex virus type 1 or 2 and human cytomegalovirus. For the purposes of this invention, the HBNF protein and MK protein may be derived from native sources, i.e., a purified protein, or it may be recombinantly derived. In the preferred embodiment of this invention, the HBNF and MK proteins are human HBNF and MK, but analogous proteins isolated and recombinantly derived from other animals are also encompassed by this invention. Recombinantly derived means produced from an autonomous nucleic acid that is introduced into an appropriate host cell and transcribed and/or translated into protein product and subsequently isolated. The HBNF protein and MK protein of this invention include all analogs, allelic variants and derivatives of naturally occurring and recombinantly produced HBNF and MK proteins.

For the purposes of this invention, the term "pharmaceutically acceptable carrier" encompasses any of the standard pharmaceutical or ophthalmic carriers, such as phosphate buffered saline solution, water, methyl cellulose, polyethylene glycol, DMSO and liposomes. The term "the virus being characterized by the presence of heparin-binding protein" encompasses viral proteins that bind to the cell surface heparan sulfate proteoglycans present on a cell surface. For example, herpes simplex viral glycoproteins (HSP) gB and gC bind cell surface heparan sulfate proteoglycans.

The effective amount of the active ingredient, HBNF, MK or a combination of both and other anti-viral agents, is any amount which will inhibit viral infectivity of a cell either by binding to the cellular HSP or by binding to the viral proteins capable of interaction with HSP. These amounts will vary depending on the intended use, the viral infection being treated or prevented, mode of administration as well as other characteristics of the subject being treated. Persons skilled in the art will be readily able to determine such amounts.

This invention also provides a method of inhibiting the infectivity or preventing the infection of a virus, the virus being characterized by the presence of a heparin-binding protein. This method comprises contacting the cellular receptor for the virus or the receptor-binding protein of the virus with an effective amount of any of the compositions described hereinabove. The terms "being characterized by the presence of a heparin-binding protein" and "effective amount" also have been described hereinabove. In the preferred method, the virus is a Herpesviridae virus. In the most preferred method, the Herpesviridae virus is a herpes simplex virus or a human cytomegalovirus.

These methods are particularly effective when the subject is an animal, such as a human, mouse, rat, cow, horse, pig or fowl. However, in the most preferred embodiment, a human being is treated.

For example, this invention will be useful to treat or prevent cytomegaloviral infections of the eye in Acquired Immune Deficiency Syndrome ("AIDS") patients as well as cold sores and genital herpes in other patients. In these instances, the pharmaceutical composition is topically applied to the affected or likely to be affected area. For example, the composition may be administered to the subject's eye in an eye drop, or applied to the lips via an ointment. Alternatively, when the composition is to be administered systemically, the administration may be, but is not limited to, administration orally, intramuscularly, intravenously, in slow-releasing capsule form and by osmotic pump. An effective amount may comprise from about 1 μg/kg body weight to about 100 mg/kg body weight of the subject. However, in the preferred embodiment of this invention, a dose of about 0.1 mg/kg to about 10 mg/kg body weight of the subject will be administered. As is known to those of skill in the art, the exact amount administered depends on the infection being treated or prevented as well as other physical characteristics of the subject.

The experiments described below are for illustration purposes only, and are not meant to limit the scope of the invention claimed herein.

MATERIALS AND METHODS

Cloning and Sequencing of the MK Gene

The published mouse MK portein amino acid sequence was used to create specific oligonucleotides to be used as primers in a polymerase chain reaction. Mouse genomic DNA was isolated from C57 Black/6J mice, as described in Maniatis (38).

A sense primer is made to the amino acid sequence: (positions 52 to 59 of Sequence ID No. 1) CNWKKEFG (FIG. 1) starting with a HindIII restriction site and comprised of the DNA sequence:

5' GGAATTCGGTCTCCTGGCACTGGGCAGT-3'.

The polymerase chain reaction (PCR) is carried out on the complementary DNA template with a one minute annealing at 50° C., 2 minutes extension at 72° C. and 1 minute denaturation at 94° C. for 30 cycles using Taq polymerase (USB Corp.)

The 150 base pair mouse MK PCR product is cloned into Blue Scribe (+) vector (Stratagene) and used as a probe in screening a newborn brain stem and basal ganglia λ gt 11 cDNA library (39). A single putative clone containing the MK sequence is isolated and subcloned into the EcoRI site of Blue Scribe (+) and sequenced by the dideoxynucleotide chain termination method (40). The sequence of the MK gene, as well as the predicted amino acid sequence is presented in FIG. 1. Comparison with the mouse MK sequence shows a 41 nucleotide difference, including the three codon deletion in the mouse sequence.

Expression of Recombinant Human MK

The isolated clone noted above, referred to as pMKHC2 is used as a template for PCR amplification with primers designed to place a methionine codon and an Nde I restriction site immediately 5' to the N-terminal lysine. The purified PCR product is cloned into a derivative of the expression vector pET-3a, which is modified by the deletion of the 1400 bp SalI/PvuII fragment and insertion of an f1 origin of replication into the EcoRI site. After sequencing the insert to confirm the fidelity of the PCR amplification, the plasmid (named pETMH2; also previously referred to as pET-MKHC2) is transformed into strain BL21 lysS and induced for protein production with IPTG. Pellets from one ml culture are resuspended in 100 μl of SDS buffer (41) and 2.5 μl run on a 15% acrylamide SDS-PAGE gel. The gel is stained with coomassie blue. Recombinant MK is purified from bacterial extract on heparin sepharose CL-6B (Pharmacia) resin in 10 mM Tris, pH 7.0 and eluted at 1–1.13M NaCl. Further purification is achieved on Mono S (Pharmacia) columns in 50 mM sodium phosphate, pH 6.8, with increasing salt concentration from 0 to 1M NaCl. Purified protein is eluted at 0.6M NaCl.

Cloning and Sequencing of the HBNF Gene

The human DNA sequence encoding HBNF was cloned by utilizing a combination of polymerase chain reaction (PCR) and screening of a cDNA library derived from newborn human brainstem cells. Bovine HBNF amino acid sequence was used as a starting point for designing oligoucleotides for a PCR amplification reaction. A partial 114 amino acid sequence of bovine HBNF is provided in FIG. 2. It is expected that the total length of the protein is 136 amino acids, as is the human protein. Poly (A)+RNA from adult rat brain is reverse transcribed to produce a complementary cDNA strand. This strand was then used as a template for the PCR reaction, with sequence specific primers. The expected 282 base pair PCR product was then isolated and cloned into an appropriate vector. DNA sequencing identifies the cloned fragment that encodes the rat HBNF peptide. The cloned insert was isolated, labeled, and used as a probe to screen a phage cDNA library. Of approximately a million and a half phage screened, four candidate cDNA clones were isolated, subcloned and sequenced. The DNA sequence of human HBNF is presented in FIG. 3B.

The cDNA sequence indicates that the human HBNF protein is 136 amino acids long. There is a single amino acid difference from the bovine sequence, at residue 98 (Asp in bovine, Glu in human). On the basis of N-terminal protein and cDNA complete sequence information, the expected molecular weight of the protein would be 15 kD, which is smaller than the 18 kD protein previously observed with SDS-PAGE (42, 43). Therefore, it is assumed that the observed size difference is due to the effect of the basicity of the protein on its migration on the gel.

Also, two smaller forms of the human protein had been previously identified (EP 326 075); these probably represent C-terminal truncated forms of the full length protein generated by change during extraction/isolation when enzyme inhibitors are absent. A putative methionine translation initiation codon is located 32 amino acids preceding the N-terminal glycine of the mature protein; this presequence is not similar to previously identified signal sequences. (44). However, if translation of the protein is initiated at this methionine, the presequence would represent the only hydrophobic region in an otherwise highly hydrophilic protein. The protein processing site preceding the mature HBNF protein, agrees with structural determinants for cleavage of a signal sequence from a mature protein (51).

Figure 4:
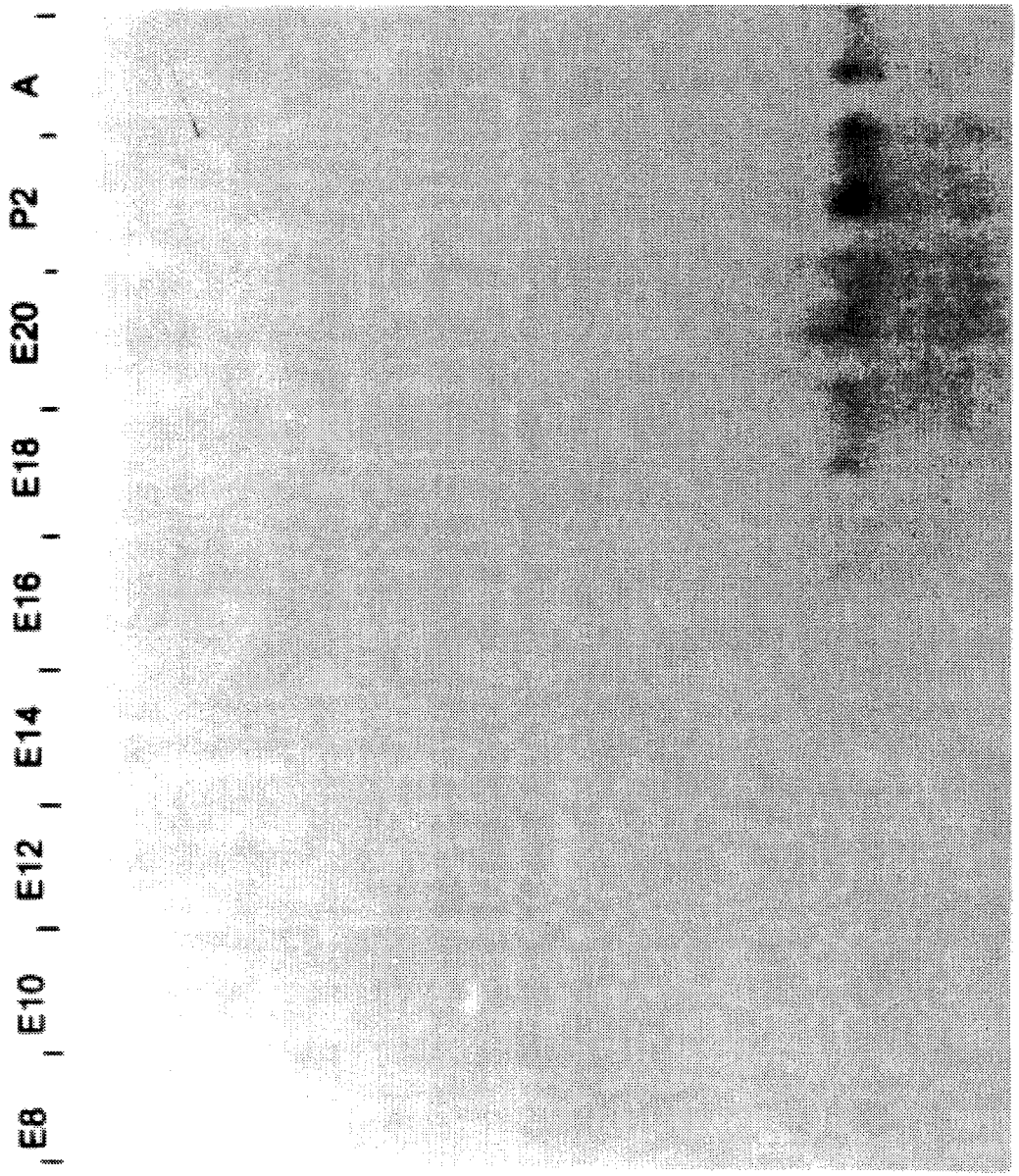
FIG. 4 illustrates expression and functional characterization of human HBNF protein. (a) SDS-PAGE gel electrophoresis of HBNF protein samples. Protein standards were from BRL. Lane N, purified bovine HBNF protein (100 ng), Lanes+and–isopropyl-β-D-thio-galactopyronoside (IPTG) induced and uninduced cultures containing the bacterial expression construct pETHHS.

To provide a source of mature human HBNF protein free of contaminating eukaryotic proteins one of the clones, HHC8 was used as template for PCR amplification with primers designed to place a methionine codon immediately 5' to the N-terminal glycine (FIG. 3b). The amplified product is cloned into a modified form of the expression vector pET-3a (45) and the resulting plasmid, pETHH8 transformed into strain BL21 LysS (id.). A protein extract of the IPTG-induced culture containing pETHH8 (FIG. 4a lane 3) shows a strong protein band approximately the same size as mature bovine HBNF (lane 1), compared to a faint protein band at the corresponding position for the uninduced culture (lane 2). The fact that bacterially produced HBNF migrates in the same position on SDS-PAGE as bovine and rat-derived HBNF and is biologically active, suggests that there is minimal, if any, posttranslational modification(s) of the native HBNF protein as compared to HBNF expressed in E. coli. The lack of a recognizable glycosylation signal in the HBNF sequence further supports this hypothesis.

Human HBNF protein is purified from IPTG-induced bacterial cultures by utilizing its affinity for heparin. Its N-terminal amino acid sequence is confirmed by protein sequencing and the protein is assayed for neurotrophic activity in a neurite outgrowth assay. This bacterially derived human HBNF showed activity comparable to that of bovine and rat HBNF. Thus, consistent with observations described above, it was found that mature HBNF has neurotrophic activity.

The following examples illustrate the cloning and expression of the HBNF gene in a T7 RNA polymerase expression system. However, although this T7 expression system has proven quite efficient, it is to be understood that this is not the only means by which human HBNF can be produced recombinantly. Production of HBNF can be achieved by incorporation of the HBNF gene into any suitable expression vector and subsequent transformation of an appropriate host cell with the vector; alternatively the transformation of the host cells can be achieved directly by naked DNA without the use of a vector. Production of HBNF by either eukaryotic cells or prokaryotic cells is contemplated by the present invention. Examples of suitable eukaryotic cells include mammalian cells, plant cells, yeast cells and insect cells. Similarly, suitable prokaryotic hosts in addition to E. coli, include Bacillus subtilis.

Other suitable expression vectors may also be employed and are selected based upon the choice of host cell. For example, numerous vectors suitable for use in transforming bacterial calls are well known. For example, plasmids and bacteriophages, such as λ phage, are the most commonly used vectors for bacterial hosts, and for E. coli in particular. In both mammalian and insect cells, virus vectors are frequently used to obtain expression of exogenous DNA. In particular, mammalian cells are commonly transformed with SV40 or polyoma virus; and insect cells in culture may be transformed with baculovirus expression vectors. Yeast vector systems include yeast centromere plasmids, yeast episomal plasmids and yeast integrating plasmids.

It will also be understood that the practice of the invention is not limited to the use of the exact sequence of the human MK or HBNF gene, as defined in FIGS. 1 and 3, respectively. Modifications to the sequence, such as deletions, insertions, or substitutions in the sequence which produce silent changes in the resulting protein molecule are also contemplated. For example, alteration in the gene sequence which reflect the degeneracy of the genetic code, or which result in the production of a conservative amino change at a given site, are contemplated. Similarly, changes which result in substitution of one negatively charged residue for another can also be expected to produce a biologically equivalent product. Additionally, since it is primarily the central portion of the protein which is conserved among species, nucleotide changes which result in alteration of the N-terminal and C-terminal portions of the protein molecule, would not be expected to alter the activity of the protein.

Indeed, the "HBBM" size variants disclosed in EP 326, 075 include C-terminal truncation of the HBNF protein. It may also be desirable to eliminate one or more of the cysteines present in the sequence, as a way of modifying the activity of the protein. Each of the proposed modifications is well within the routine skill in the art, as is determination of retention of biological activity of the encoded products. Therefore, where the phrase "DNA sequence" or "gene" is used, it will be understood to encompass all such modifications and variations which result in the production of a biologically equivalent protein. In particular, the invention contemplates those DNA sequences which are sufficiently duplicative of the sequences of FIGS. 1 and 3 so as to permit hybridization therewith under standard high stringency southern hybridzation conditions, such as those described in Maniatis et al., (38)

HBNF Protein Purification and Amino Acid Sequence Analysis

Figure 5:
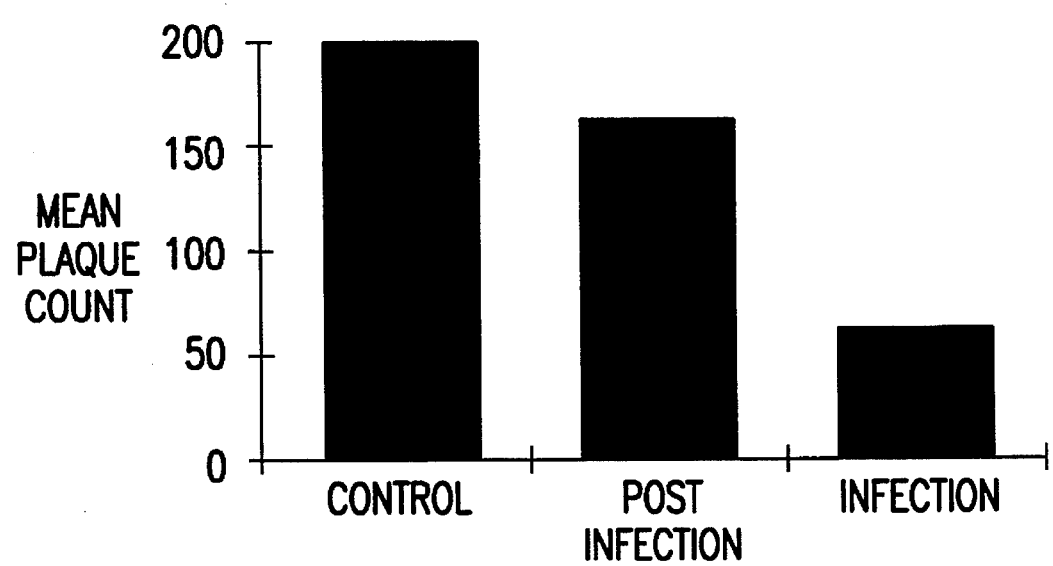
FIG. 5. Effect of time of HBNF Addition on HSV-1 Plaque Formation. Confluent monolayers of Vero cells in 6-well dishes were infected with 200 PFU per well of HSV-1 strain as described. Control samples were infected without HBNF during the virus adsorption period or in the overlay. Postinfection—samples were infected without HBNF during virus adsorption but HBNF was added to the overlay at a final concentration of 4.25 μg/ml. Infection—samples were infected with virus in the presence of 4.25 μg/ml of HBNF and HBNF was added to the overlay at the same concentration.

HBNF protein is isolated from bovine brain by protocols described previously in EP 326 075, which is incorporated herein by reference in its entirety. Briefly, reverse-phase HPLC-purified HBNF is chemically modified by reduction in mercaptoethanol and alkylation of cysteine residues with iodo-(2-14C)-acetic acid according to a procedure described previously (46). Carboxymethylated protein is purified by reverse-phase HPLC using a Brownlee Aquapore C8 column (25×0.46 cm 7 µm particle size, Applied Biosystems) using as the mobile phase 0.1% trifluorocetic acid in an acetonitrile gradient. Aliquots corresponding to 3 nmol of carboxymethylated HBNF are diluted with enzyme digestion buffer to reduce the acetonitrile concentration of the sample to approximately 10% and digested with the following proteases: *Staphylococcus aureus* V8 (cleavage after glutamic acid residues), Arg-C (cleavage after arginine), Asp-N (cleavage before aspartic acid) and chymotrypsin (preferential cleavage after aromatic residues). Enzymes are from Boehringer Mannheim and cleavage is performed essentially as suggested by the manufacturer. After digestion, peptides are separated by reverse-phase HPLC on a C8 column using a 90-min linear gradient of acetonitrile in 0.1% trifluoroacetic acid for peptide elution (acetonitrile content at start: 12–16%, at end: 30–44%, depending on the type of digest). In order to ascertain homogeneity of purified peptides, fractions containing peptide material are subjected to a second reverse-phase HPLC step (C8 column, 0.1% heptafluorobutyric acid in an appropriate shallow acetonitrile gradient). Aliquots of 5–500 pmol of isolated peptides are sequenced on an Applied Biosystems 477A gas/liquid-phase microsequenator. Phenyl thiohydantoin (PTH) amino acid derivatives are identified on a Model 120A on-line PTH amino acid analyzer (Applied Biosystems). Experimental protocols for both procedures are as supplied by the instrument manufacturer. The sequence of the first 114 amino acids (out of an expected 136) is shown in FIG. 5.

Polymerase Chain Reaction (PCR)

The bovine HBNF amino acid sequence is used to design degenerate oligonucleotides from the PCR amplification reaction. A completely degenerate sense primer is made to the amino acid sequence (positions 14 to 20 of sequence ID No. 4): DCGEWOW (FIG. 3) starting with a HindIII restriction site and comprised of the DNA sequence:

5'-CAAGCTTGGAPyTGPIGGNGAPuTGGCAPuTGG-3'.

A completely degenerate antisense primer is made to the amino acid sequence (positions 96 to 102 of sequence ID No. 4): NADCQKT (FIG. 3) starting with an EcoRI restriction site and comprised of the DNA sequence:

5'-GGAATTCCGTPyTTPyTGPuCAPuTCNGCPuTT-3'

Total rat brain RNA is isolated from the brains of Sprague-Dawley rats by the guanidinium isothiocyanatecesium chloride method and poly (A)+RNA is selected by two cycles of binding to oligo (dT)–cellulose (47). The rat brain poly (A)+RNA is reverse transcribed with oligo (dt) and AMV-reverse transcriptase (38) The PCR reaction is carried out on the complementary DNA template, with 30 cycles, with one minute annealing at 50° C., two minutes extension at 72° C. and one minute denaturation at 94° C. for 30 cycles using Taq DNA polymerase (USB).

Cloning and Sequencing of Human HBNF

The 282 base pair rat HBNF PCR product is cloned into Blue Scribe (+) vector (Stratagene) and used as a probe in screening a newborn human brainstem and basal ganglia λ gt 11 cDNA library (48). Thirty HHC clones are initially identified and after preliminary restriction analysis, four clones are isolated, subcloned in the EcoRI site of Blue Scribe (+), and sequenced by the dideoxynucleotide chain termination method (49).

Three of the clones have identical sequences in the coding region and the fourth clone has a three-nucleotide in-frame deletion resulting in the removal of an alanine at position 119. These sequences are illustrated in FIG. 3.

Expression of Recombinant HBNF

Clone HHC8 (FIG. 3a) is chosen for use as a template for PCR amplification with primers designed to place a methionine codon and an NdeI restriction site immediately 5' to the N-terminal glycine. The purified PCR product is cloned into a derivative of the expression vector pET-3a, which is modified by the deletion of the 1400 bp SalI/PvuII fragment and insertion of an f1 origin of replication into the EcoRI site. After sequencing the insert to confirm the fidelity of the PCR amplification, the plasmid (named pETHH8) is transformed into strain BL21 lysS and induced for protein production with IPTG as described (45). Pellets from one ml cultures are resuspended in 100 ul of SDS buffer (50) and 2.5 ul run on a 15% acrylamide SDS-PAGE gel. The gel is stained with coomassie blue. Native HBNF is purified from rat brains and recombinant HBNF from bacterial extract on heparin sepharose CL-6B (Pharmacia) resin in 10 mM Tris, pH 7.0 and eluted with a gradient from 0–2M NaCl at 1–1.13M NaCl. Further purification is achieved on Mono S (Pharmacia) columns in 50 mM sodium phosphate, pH 6.8, using a gradient of increasing salt concentration from 0 to 1M NaCl for elution.

Antiviral Activity

Cells and virus. Vero cells were obtained from ATCC and maintained in Dulbecco's modified Eagle medium (Mediatech) containing 10% calf serum (Cell Culture Laboratories), 25 mM HEPES (N-2-hydroxyethylpiperazine-N'-2-ethanesulfonic acid and antibiotics: penicillin G 50 units/ml and streptomycin 50 mg/ml (Gibco). Human foreskin fibroblasts (HFF) were isolated in this laboratory and were maintained in high glucose (4.5 mg/ml) Dulbecco's modified Eagle medium (Mediatech) containing 10% fetal bovine serum (Cell Culture Laboratories); other modifications were as described above. Virus growth medium is essentially as described except that 2% fetal bovine serum was used for both HSV and HCMV infections. HSV-1 strain CJ 360 and HSV-2 strain 333 (27) were obtained from Dr. C. Brandt (The University of Wisconsin). HCMV strain Towne was obtained from ATCC.

Virus infections. HSV stocks were prepared by infection of Vero cell monolayers in 225 cm² flasks at a multiplicity of 0.01 PFU/cell in phosphate-buffered saline (PBS) containing 2% fetal bovine serum. After virus adsorption for 1 hour at 37° C., the virus inoculum was removed and replaced with virus growth medium as described above. Infection was allowed to proceed until 100% of the cells were infected as judged by microscopic examination. Virus was harvested by scraping cells into the supernatant medium and subjecting to three freeze-thaw cycles. Cell debris was removed from the virus suspension by centrifugation for 10 minutes at 1,000 rpm at 4° C. HCMV stocks were prepared in HFF cells essentially as described for HSV except that virus growth medium was replaced every third day until infection of the monolayer was complete. Cells for virus plaque assay were infected by diluting stock virus in PBS containing 2% fetal bovine serum and applying 1 ml of the virus inoculum to Vero cell (HSV) or HFF (HCMV) monolayers. Virus was allowed to adsorb to cells for 1 hour at 37° C. at which time the virus inoculum was removed and the cells rinsed once with PBS and then overlayered with modified essential medium (Gibco) containing 2% fetal bovine serum and 1.0% agarose. Monolayers were fixed and stained by addition of 20% trichloroacetic acid (TCA) on the agarose plug; after 10 minutes the TCA was aspirated and the agarose removed from the wells, the fixed monolayer was then stained with a 0.1% crystal violet solution containing 20% methanol and 2% formaldehyde.

The 50% inhibitory concentrations were determined by calculating efficiencies of virus plaque formation in the presence of varying concentrations of protein factor relative to infected, untreated controls by the methods described. The median effect dose was calculated using the Median Dose Effect Plot Program (Elsevier Biosoft) as described by Chou (28).

Proteins. Human, platelet-derived PF4 was purchased from Sigma (St. Louis). Recombinant HBNF and MK proteins were expressed and purified as described hereinabove (29). Carboxymethylated HBNF was prepared as follows: Lyophilized recombinant HBNF was dissolved in 0.1M Tris-HCl pH 8.6, containing 2 mM EDTA and 4.5M guanidinium HCl to give a concentration of 0.5 mg/ml. The protein was reduced with dithiothreitol (5 mM) and the solution incubated under an argon atmosphere for 1 hour at 37° C. The reduced protein solution was cooled to room temperature and alkylated using iodoacetic acid (15 mM) for 1 hour in the dark. The carboxymethylated protein was dialysed (3500 molecular weight cut-off) overnight at 4° C. versus 10 mM Tris-HCl pH 7.2 containing 200 mM NaCl. Carboxymethylcysteine and protein concentrations were determined by amino acid analysis after HCl gas phase hydrolysis (5.7M HCl/0.1% phenol; 24 h at 110° C.) using a model 420A PITC-derivatizer equipped with an on-line model 130A separation system (Applied Biosystems, CA). Carboxymethylated HBNF was eluted from Heparin-sepharose with 0.6M NaCl.

Antiviral Results

HBNF and MK were tested for antiviral activity against HSV-1 and HCMV by measuring enzyme activity of recombinant viruses genetically engineered to express bacterial β-glucuronidase (as will be described separately). HBNF and MK were found to inhibit HSV and HCMV with 50% inhibitory concentrations of 4 µg/ml and 2 µg/ml respectively. No virus inhibitory activity of HBNF against influenza A virus could be demonstrated using an ELISA assay suggesting that the effects observed against herpes viruses were specific and not directed against enveloped viruses in general.

The effects of HBNF and MK on wild type HSV and HCMV infection of Vero cells were further assayed using a plaque assay and found that both proteins inhibited infectivity of these viruses (Table 1). The $IC_{50}$ for both proteins were in the submicromolar range and HSV-2 appeared to be less sensitive than HSV-1 or HCMV (Table 1). Infectivity of HSV was also inhibited by platelet factor PF4, another heparin-binding protein, with $IC_{50}$ similar to that of HBNF and MK (Table 1). The inhibitory activity of HBNF was destroyed by carboxymethylation of the protein's ten cysteine residues. This treatment, presumably, prevents proper folding of HBNF and eliminates two other activities of HBNF: the ability to prevent bFGF binding to high affinity receptors and an anti-proliferative activity directed towards endothelial cells (26).

Subsequently, the antiviral action of HBNF was determined. Vero cells were infected with HSV-1 either in the presence of HBNF, or without HBNF. During initial viral adsorption HBNF was then added in the overlay in both systems. The results of this experiment clearly indicate that antiviral activity of HBNF was significant only when it was present during viral adsorption (FIG. 5).

Discussion

In this invention, it is reported that the two recombinant human heparin-binding proteins HBNF and MK inhibit HSV and HCMV infectivity. This effect is, apparently, due to the inhibition of viral adsorption on the target cells. Similar activities were recently reported for two heparin-binding proteins: human platelet-derived PF4 (1) and human bFGF (17, 20).

HBNF and MK, bFGF, and PF4 belong to different protein families and thus direct competition for binding to the putative high affinity viral receptor seems unlikely. However, all four proteins, may compete with virus for binding to the heparan sulfate moieties of cell surface HSP. Although there are known high affinity receptors for bFGF (30–36), it was discovered, recently, that bFGF binds to cell surface HSP in order to acquire an "induced fit" conformation which is able to bind to high affinity receptors (22–24). Thus, bFGF may inhibit viral adsorption by occupying cell surface HSP, rather then high affinity receptors.

The affinities of HBNF and MK for cellular HSP are not known. Affinity of human PF4 for HSP of bovine endothelial cells was recently characterized ($K_d$=2.87 µM, 37). If HBNF, MK and PF4 have similar affinities for heparan sulfate, one would expect that micromolar or submicromolar concentrations of these proteins would saturate cell surface HSP and inhibit HSV and HCMV infectivity.

Currently, most of available drugs effective against HSV and CMV infections are low-molecular weight compounds. These drugs are given systemically and some of them have a high degree of toxicity, particularly in immunocompromised patients.

Heparin binding proteins are antiviral agents which act to block infectivity of members of the herpes virus family. As such, these proteins are useful in a variety of disease states caused by herpes viruses especially the alpha herpes viruses, herpes simplex types 1 and 2 and varicella zoster virus, and the beta herpes virus, cytomegalovirus. A particular hallmark of the herpes viruses is their propensity to cause latent infections which can be reactivated at times subsequent to resolution of the initial acute infection. Because the heparin binding proteins block the infectivity of virus at the level of the cellular receptor, they would not be expected to inhibit reactivation of virus per se. Rather, these proteins would prevent virus infection and spread at distal sites of virus replication. This approach to therapy would be applicable to reactivated virus infections such as cold sores, recurrent genital herpes, ocular infections caused particularly by herpes simplex and cytomegalovirus as well as zosteriform rash in herpes zoster. Treatment with recombinant heparin binding is also useful in limiting the spread of virus during initial acute infection and can also be considered as prophylactic therapy in the immunocompromised host where opportunistic herpes virus infection is a severe problem.

TABLE 1

Antiviral Activity of HBNF and Related Factors

| | $IC_{50}$ (µg/ml) | | |
|---|---|---|---|
| | HSV-1 | HSV-2 | HCMV |
| HBNF | 1.6 | 5.8 | 1.5 |

TABLE 1-continued

Antiviral Activity of HBNF and Related Factors

| | $IC_{50}$ (µg/ml) | | |
|---|---|---|---|
| | HSV-1 | HSV-2 | HCMV |
| MK | 1.9 | 4.2 | — |
| PF-4 | 1.0 | ND | ND |

Virus plaque reduction assays were performed as described in Materials and Methods. Vero cells in six well cluster dishes were infected with virus at an input multiplicity of 200 PFU/well in the presence of various concentrations of protein factor. Plaquing efficiencies in factor treated cultures were calculated relative to infected untreated controls and the 50% inhibitory concentration determined using the Median Dose Effect program.

SEQUENCE LISTING ( 1 ) GENERAL INFORMATION:

( i i i ) NUMBER OF SEQUENCES: 5

( 2 ) INFORMATION FOR SEQ ID NO: 1:

( i ) SEQUENCE CHARACTERISTICS:
        ( A ) LENGTH: 799 Base Pairs
        ( B ) TYPE: Nucleic Acid
        ( C ) STRANDEDNESS: Single
        ( D ) TOPOLOGY: Linear ( i i ) MOLECULE TYPE: DNA (genomic)

( i x ) FEATURE:
        ( A ) NAME/KEY: CDS
        ( B ) LOCATION: 26..457

( x i ) SEQUENCE DESCRIPTION: SEQ ID NO: 1:

```
CGGGCGAAGC  AGCGCGGGCA  GCGAG                                           25

ATG  CAG  CAC  CGA  GGC  TTC  CTC  CTC  CTC  ACC  CTC  CTC            61
Met  Gln  His  Arg  Gly  Phe  Leu  Leu  Leu  Thr  Leu  Leu
 1                   5                        10

GCC  CTG  CTG  GCG  CTC  ACC  TCC  GCG  GTC  GCC  AAA  AAG            97
Ala  Leu  Leu  Ala  Leu  Thr  Ser  Ala  Val  Ala  Lys  Lys
         15                       20

AAA  GAT  AAG  GTG  AAG  AAG  GGC  GGC  CCG  GGG  AGC  GAG           133
Lys  Asp  Lys  Val  Lys  Lys  Gly  Gly  Pro  Gly  Ser  Glu
 25                  30                       35

TGC  CGT  GAG  TGG  GCC  TGG  GGG  CCC  TGC  ACC  CCC  AGC           169
Cys  Arg  Glu  Trp  Ala  Trp  Gly  Pro  Cys  Thr  Pro  Ser
             40                       45

AGC  AAG  GAT  TGC  GGC  GTG  GGT  TTC  CGC  GAG  GGC  ACC           205
Ser  Lys  Asp  Cys  Gly  Val  Gly  Phe  Arg  Glu  Gly  Thr
         50                       55                   60

TGC  GGG  GCC  CAG  ACC  CAG  CGC  ATC  CGG  TGC  AGG  GTG           241
Cys  Gly  Ala  Gln  Thr  Gln  Arg  Ile  Arg  Cys  Arg  Val
                     65                       70

CCC  TGC  AAC  TGG  AAG  AAG  GAG  TTT  GGA  GCC  GAC  TGC           277
Pro  Cys  Asn  Trp  Lys  Lys  Glu  Phe  Gly  Ala  Asp  Cys
             75                       80
```

```
AAG TAC AAG TTT GAG AAC TGG GGT GCG TGT GAT GGG              313
Lys Tyr Lys Phe Glu Asn Trp Gly Ala Cys Asp Gly
 85              90                  95

GGC ACA GGC ACC AAA GTC CGC CAA GGC ACC CTG AAG              349
Gly Thr Gly Thr Lys Val Arg Gln Gly Thr Leu Lys
            100                 105

AAG GCG CGC TAC AAT GCT CAG TGC CAG GAG ACC ATC              385
Lys Ala Arg Tyr Asn Ala Gln Cys Gln Glu Thr Ile
    110              115                 120

CGC GTC ACC AAG CCC TGC ACC CCC AAG ACC AAA GCA              421
Arg Val Thr Lys Pro Cys Thr Pro Lys Thr Lys Ala
                125             130

AAG GCC AAA GCC AAG AAA GGG AAG GGA AAG GAC TAG              457
Lys Ala Lys Ala Lys Lys Gly Lys Gly Lys Asp Xaa
        135             140

ACGCCAAGCC TGGATGCCAA GGAGCCCTG GTGTCACATG                   497

GGGCCTGGCC ACGCCCTCCC TCTCCCAGGC CGAGATGTG                   537

ACCCACCAGT GCCTTCTGTC TGCTCGTTAG CTTTAATCAA                  577

TCATGCCCTG CCTTGTCCCT CTCACTCCCC AGCCCCACCC                  617

CTAAGTGCCC AAAGTGGGGA GGGACAAGGG ATTCTGGGAA                  657

GCTTGAGCCT CCCCCAAAGC AATGTGAGTC CCAGAGCCCG                  697

CTTTTGTTCT TCCCCACAAT TCCATTACTA AGAAACACAT                  737

CAAATAAACT GACTTTTTCC CCCCAATAAA AGCTCTTCTT                  777

TTTTAATATA AAAAAAAAA AA                                      799
```

( 2 ) INFORMATION FOR SEQ ID NO: 2:

( i ) SEQUENCE CHARACTERISTICS:
        ( A ) LENGTH: 144 Amino Acids
        ( B ) TYPE: Amino Acid
        ( D ) TOPOLOGY: Linear ( i i ) MOLECULE TYPE: Protein ( x i ) SEQUENCE DESCRIPTION: SEQ ID NO: 2:

```
Met Gln His Arg Gly Phe Leu Leu Leu Thr Leu Leu
 1               5                    10

Ala Leu Leu Ala Leu Thr Ser Ala Val Ala Lys Lys
            15              20

Lys Asp Lys Val Lys Lys Gly Gly Pro Gly Ser Glu
 25              30                  35

Cys Ala Glu Trp Ala Trp Gly Pro Cys Thr Pro Ser
            40              45

Ser Lys Asp Cys Gly Val Gly Phe Arg Glu Gly Thr
    50              55                  60

Cys Gly Ala Gln Thr Gln Arg Ile Arg Cys Arg Val
            65                  70

Pro Cys Asn Trp Lys Lys Glu Phe Gly Ala Asp Cys
        75              80

Lys Tyr Lys Phe Glu Asn Trp Gly Ala Cys Asp Gly
 85              90                  95

Gly Thr Gly Thr Lys Val Arg Gln Gly Thr Leu Lys
            100             105

Lys Ala Arg Tyr Asn Ala Gln Cys Gln Gly Thr Ile
```

|   |   |   |   |   |   |   |   |   |   |   |
|---|---|---|---|---|---|---|---|---|---|---|
| | | | 110 | | | 115 | | | 120 | |
| Arg | Val | Thr | Lys | Pro | Cys | Thr | Pro | Lys | Thr | Lys | Ala |
| | | | | 125 | | | | 130 | | |
| Lys | Ala | Lys | Ala | Lys | Lys | Gly | Lys | Gly | Lys | Asp | Xaa |
| | | 135 | | | | 140 | | | | 144 |

( 2 ) INFORMATION FOR SEQ ID NO: 3:

( i ) SEQUENCE CHARACTERISTICS:
        ( A ) LENGTH: 1383 Base Pairs
        ( B ) TYPE: Nucleic Acid
        ( C ) STRANDEDNESS: Single
        ( D ) TOPOLOGY: Linear ( i i ) MOLECULE TYPE: DNA (genomic)

( i i i ) ORIGINAL SOURCE:
        ( A ) ORGANISM: Homo sapiens ( i x ) FEATURE:
        ( A ) NAME/KEY: CDS
        ( B ) LOCATION: 477..983
        ( C ) OTHER INFORMATION: From Amino Acid Residue
            33 to Amino Acid Residue 168 - Mature Protein ( x i ) SEQUENCE DESCRIPTION: SEQ ID NO: 3:

| | | | | |
|---|---|---|---|---|
| AAGTAAATAA | ACTTTAAAAA | TGGCCTGAGT | TAAGTGTATT | 40 |
| AAAAAGAAGA | AATAGTCGTA | AGATGGCAGT | ATAAATTCAT | 80 |
| CTCTGCTTTT | AATAAGCTTC | CCAATCAGCT | CTCGAGTGCA | 120 |
| AAGCGCTCTC | CCTCCCTCGC | CCAGCCTTCG | TCCTCCTGGC | 160 |
| CCGCTCCTCT | CATCCCTCCC | ATTCTCCATT | TCCCTTCCGT | 200 |
| TCCCTCCCTG | TCAGGGCGTA | ATTGAGTCAA | AGGCAGGATC | 240 |
| AGGTTCCCCG | CCTTCCAGTC | CAAAAATCCC | GCCAAGAGAG | 280 |
| CCCCAGAGCA | GAGGAAAATC | CAAAGTGGAG | AGAGGGGAAG | 320 |
| AAAGAGACCA | GTGAGTCATC | CGTCCAGAAG | GCGGGGAGAG | 360 |
| CAGCAGCGGC | CCAAGCAGGA | GCTGCAGCGA | GCCGGGTACC | 400 |
| TGGACTCAGC | GGTAGCAACC | TCGCCCCTTG | CAACAAAGGC | 440 |
| AGACTGAGCG | CCAGAGAGGA | CGTTTCCAAC | TCAAAA | 476 |

| ATG | CAG | GCT | CAA | CAG | TAC | CAG | CAG | CAG | CGT | CGA | AAA | 512 |
|---|---|---|---|---|---|---|---|---|---|---|---|---|
| Met | Gln | Ala | Gln | Gln | Tyr | Gln | Gln | Gln | Arg | Arg | Lys | |
| 1 | | | | 5 | | | | | 10 | | | |

| TTT | GCA | GCT | GCC | TTC | TTG | GCA | TTC | ATT | TTC | ATA | CTG | 548 |
|---|---|---|---|---|---|---|---|---|---|---|---|---|
| Phe | Ala | Ala | Ala | Phe | Leu | Ala | Phe | Ile | Phe | Ile | Leu | |
| | | 15 | | | | | 20 | | | | | |

| GCA | GCT | GTG | GAT | ACT | GCT | GAA | GCA | GGG | AAG | AAA | GAG | 584 |
|---|---|---|---|---|---|---|---|---|---|---|---|---|
| Ala | Ala | Val | Asp | Thr | Ala | Glu | Ala | Gly | Lys | Lys | Glu | |
| 25 | | | | | 30 | | | | | 35 | | |

| AAA | CCA | GAA | AAA | AAA | GTG | AAG | AAG | TCT | GAC | TGT | GGA | 620 |
|---|---|---|---|---|---|---|---|---|---|---|---|---|
| Lys | Pro | Glu | Lys | Lys | Val | Lys | Lys | Ser | Asp | Cys | Gly | |
| | | | 40 | | | | | 45 | | | | |

| GAA | TGG | CAG | TGG | AGT | GTG | TGT | GTG | CCC | ACC | AGT | GGA | 656 |
|---|---|---|---|---|---|---|---|---|---|---|---|---|
| Glu | Trp | Gln | Trp | Ser | Val | Cys | Val | Pro | Thr | Ser | Gly | |
| | 50 | | | | | 55 | | | | | 60 | |

| GAC | TGT | GGG | CTG | GGC | ACA | CGG | GAG | GGC | ACT | CGG | ACT | 692 |
|---|---|---|---|---|---|---|---|---|---|---|---|---|
| Asp | Cys | Gly | Leu | Gly | Thr | Arg | Glu | Gly | Thr | Arg | Thr | |
| | | | | 65 | | | | | 70 | | | |

| GGA | GCT | GAG | TGC | AAG | CAA | ACC | ATG | AAG | ACC | CAG | AGA | 728 |

|  |  |  |  |  |  |  |  |  |  |  |
|---|---|---|---|---|---|---|---|---|---|---|
| Gly | Ala | Glu | Cys | Lys | Gln | Thr | Met | Lys | Thr | Gln | Arg |
|  |  | 75 |  |  |  |  | 80 |  |  |  |  |

| TGT | AAG | ATC | CCC | TGC | AAC | TGG | AAG | AAG | CAA | TTT | GGC | 754 |
|---|---|---|---|---|---|---|---|---|---|---|---|---|
| Cys | Lys | Ile | Pro | Cys | Asn | Trp | Lys | Lys | Gln | Phe | Gly |  |
| 85 |  |  |  |  | 90 |  |  |  |  | 95 |  |  |

| GCG | GAG | TGC | AAA | TAC | CAG | TTC | CAG | GCC | TGG | GGA | GAA | 800 |
|---|---|---|---|---|---|---|---|---|---|---|---|---|
| Ala | Glu | Cys | Lys | Tyr | Gln | Phe | Gln | Ala | Trp | Gly | Glu |  |
|  |  |  | 100 |  |  |  |  | 105 |  |  |  |  |

| TGT | GAC | CTG | AAC | ACA | GCC | CTG | AAG | ACC | AGA | ACT | GGA | 836 |
|---|---|---|---|---|---|---|---|---|---|---|---|---|
| Cys | Asp | Leu | Asn | Thr | Ala | Leu | Lys | Thr | Arg | Thr | Gly |  |
|  |  | 110 |  |  |  | 115 |  |  |  |  | 120 |  |

| AGT | CTG | AAG | CGA | GCC | CTG | CAC | AAT | GCC | GAA | TGC | CAG | 872 |
|---|---|---|---|---|---|---|---|---|---|---|---|---|
| Ser | Leu | Lys | Arg | Ala | Leu | His | Asn | Ala | Glu | Cys | Gln |  |
|  |  |  |  | 125 |  |  |  |  | 130 |  |  |  |

| AAG | ACT | GTC | ACC | ATC | TCC | AAG | CCC | TGT | GGC | AAA | CTG | 908 |
|---|---|---|---|---|---|---|---|---|---|---|---|---|
| Lys | Thr | Val | Thr | Ile | Ser | Lys | Pro | Cys | Gly | Lys | Leu |  |
|  |  | 135 |  |  |  |  | 140 |  |  |  |  |  |

| ACC | AAG | CCC | AAA | CCT | CAA | GCA | GAA | TCT | AAG | AAG | AAG | 944 |
|---|---|---|---|---|---|---|---|---|---|---|---|---|
| Thr | Lys | Pro | Lys | Pro | Gln | Ala | Glu | Ser | Lys | Lys | Lys |  |
| 145 |  |  |  |  | 150 |  |  |  |  | 155 |  |  |

| AAA | AAG | GAA | GGC | AAG | AAA | CAG | GAG | AAG | ATG | CTG | GAT | 980 |
|---|---|---|---|---|---|---|---|---|---|---|---|---|
| Lys | Lys | Glu | Gly | Lys | Lys | Gln | Glu | Lys | Met | Leu | Asp |  |
|  |  |  | 160 |  |  |  |  | 165 |  |  |  |  |

| TAA |  |  | 983 |
|---|---|---|---|
| Xaa |  |  |  |
| 169 |  |  |  |

| AAGATGTCAC | CTGTGGAACA | TAAAAGGAC | ATCAGCAAAC | 1023 |
|---|---|---|---|---|
| AGGATCAGTT | AACTATTGCA | TTTATATGTA | CCGTAGGCTT | 1063 |
| TGTATTCAAA | AATTATCTAT | AGCTAAGTAC | ACAATAAGCA | 1103 |
| AAAACAACCA | ATTTGGGTTC | TGCAGGTACA | TAGAAGTTGC | 1143 |
| CAGCTTTTCT | TGCCATCCTC | GCCATTCGAA | TTTCAGTTCT | 1183 |
| GTACATCGC | CTATATTCCT | TGTGATAGTG | CTTTGCTTTT | 1223 |
| TCATAGATAA | GCTTCCTCCT | TGCCTTTCGA | AGCATCTTTT | 1263 |
| GGGCAAACTT | CTTTCTCAGG | CGCTTGATCT | TCAGCTCTGC | 1303 |
| GAAATTCCTT | CGCTTTTTCT | TAAGGGTTTC | TGGCACAGCA | 1343 |
| GGAACCTCCT | TCTTCTTCTC | TTCTACACCC | TCTATGTACC | 1383 |

( 2 ) INFORMATION FOR SEQ ID NO: 4:

( i ) SEQUENCE CHARACTERISTICS:
        ( A ) LENGTH: 169 Amino Acids
        ( B ) TYPE: Amino Acid
        ( D ) TOPOLOGY: Linear ( i i ) MOLECULE TYPE: Protein ( x i ) SEQUENCE DESCRIPTION: SEQ ID NO: 4:

| Met | Gln | Ala | Gln | Gln | Tyr | Gln | Gln | Gln | Arg | Arg | Lys |
|---|---|---|---|---|---|---|---|---|---|---|---|
| 1 |  |  |  | 5 |  |  |  |  | 10 |  |  |

| Phe | Ala | Ala | Ala | Phe | Leu | Ala | Phe | Ile | Phe | Ile | Leu |
|---|---|---|---|---|---|---|---|---|---|---|---|
|  |  | 15 |  |  |  |  | 20 |  |  |  |  |

| Ala | Ala | Val | Asp | Thr | Ala | Glu | Ala | Gly | Lys | Lys | Glu |
|---|---|---|---|---|---|---|---|---|---|---|---|
| 25 |  |  |  |  | 30 |  |  |  |  | 35 |  |

| Lys | Pro | Glu | Lys | Lys | Val | Lys | Lys | Ser | Asp | Cys | Gly |
|---|---|---|---|---|---|---|---|---|---|---|---|
|  |  |  | 40 |  |  |  |  | 45 |  |  |  |

-continued

```
Glu  Trp  Gln  Trp  Ser  Val  Cys  Val  Pro  Thr  Ser  Gly
     50                  55                       60

Asp  Cys  Gly  Leu  Gly  Thr  Arg  Glu  Gly  Thr  Arg  Thr
               65                       70

Gly  Ala  Glu  Cys  Lys  Gln  Thr  Met  Lys  Thr  Gln  Arg
          75                  80

Cys  Lys  Ile  Pro  Cys  Asn  Trp  Lys  Lys  Gln  Phe  Gly
85                       90                            95

Ala  Glu  Cys  Lys  Tyr  Gln  Phe  Gln  Ala  Trp  Gly  Glu
               100                 105

Cys  Asp  Leu  Asn  Thr  Ala  Leu  Lys  Thr  Arg  Thr  Gly
          110                 115                      120

Ser  Leu  Lys  Arg  Ala  Leu  His  Asn  Ala  Glu  Cys  Gln
                    125                      130

Lys  Thr  Val  Thr  Ile  Ser  Lys  Pro  Cys  Gly  Lys  Leu
          135                      140

Thr  Lys  Pro  Lys  Pro  Gln  Ala  Gly  Ser  Lys  Lys  Lys
145                      150                      155

Lys  Lys  Glu  Gly  Lys  Lys  Gln  Glu  Lys  Met  Leu  Asp
               160                      165

Xaa
169
```

( 2 ) INFORMATION FOR SEQ ID NO: 5:

( i ) SEQUENCE CHARACTERISTICS:
        ( A ) LENGTH: 114 Amino Acids
        ( B ) TYPE: Amino Acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO: 5:

```
Gly  Lys  Lys  Glu  Lys  Pro  Glu  Lys  Lys  Val  Lys  Lys
1                   5                        10

Ser  Asp  Cys  Gly  Glu  Trp  Gln  Trp  Ser  Val  Cys  Val
          15                  20

Pro  Thr  Ser  Gly  Asp  Cys  Gly  Leu  Gly  Thr  Arg  Glu
25                       30                       35

Gly  Thr  Arg  Thr  Gly  Ala  Glu  Cys  Lys  Gln  Thr  Met
               40                  45

Lys  Thr  Gln  Arg  Cys  Lys  Ile  Pro  Cys  Asn  Trp  Lys
     50                      55                       60

Lys  Gln  Phe  Gly  Ala  Glu  Cys  Lys  Tyr  Gln  Phe  Gln
               65                       70

Ala  Trp  Gly  Glu  Cys  Asp  Leu  Asn  Thr  Ala  Leu  Lys
          75                       80

Thr  Arg  Thr  Gly  Ser  Leu  Lys  Arg  Ala  Leu  His  Asn
85                       90                       95

Ala  Asp  Cys  Gln  Lys  Thr  Val  Thr  Ile  Ser  Lys  Pro
               100                      105

Cys  Gly  Lys  Leu  Thr  Lys
          110            114
```

65

REFERENCES

1. WuDunn, D., and Spear, P. G., J. Virol. 62:52–58, (1989).

2. Lycke, E., et al., J. Gen. Virol. 72:1131–1137 (1991).
3. Takemoto, K. K., and Fabisch, P. Proc. Soc. Exp. Biol. Med. 116:140–144 (1964).
4. Vaheri, A., Acta Pathol. Microbiol. Scan. Suppl. (Supplement) 171:7–97 (1964).
5. Nahmias, A. J., and Kibrick, S., J. Bacteriol. 87:1060–1066 (1964).
6. Langeland, et al., J. Virol. 61:3388–3393 (1987).
7. Langeland, N., et al., J. Gen. Virol. 69:1137–1145 (1988).
8. Langeland, N., et al., J. Virol. 64:1271–1277 (1990).
9. Herold, D. C., et al., J. Virol. 65:1090–1098 (1991).
10. Fuller, A. O., and Spears, P. G. Proc. Natl. Acad. Sci. USA 84:5454–5458 (1987).
11. Highlander, S. L., et al. J. Virol. 61:3356–3364 (1987).
12. Cai, W. H., et al. J. Virol. 62:714–721 (1988).
13. Ligas, M. W., and Johnson, D. C. J. Virol. 62:1486–1494 (1988).
14. Highlander, S. L., et al. J. Virol. 62:1881–1888 (1988).
15. Cranage, M. P., et al., EMBO J. 5:3057–3063 (1986).
16. Kari, B, and Gehrz, R. J. Virol. 66:1761–1764 (1992).
17. Kaner, R. J., et al., Science, 248:1410–1413 (1990).
18. Baird, A., et al., Nature (London), 348:344–346 (1990).
19. Shieh, M.-T., and Spear, P. G.. Science, 253:208–209 (1991).
20. Muugeridge, M. I., et al., J. Virol. 66:824–830 (1992).
21. Mirda, D. P., et al., J.Virol. 66:448–457 (1192).
22. Yayon, A., et al., Cell, 64:841–848 (1991).
23. Rapraeger, A. C., et al., Science (Washington DC) 252:1705–1708 (1991).
24. Ornitz, D. M., et al., Mol Cel. Biol. 12:240–247 (1992).
25. Bohlen, P., and Kovesdi, I., Prog. in Growth Factors Res. 3:143–157 (1991).
26. Backer, J., and Bohlen, P. (1991) Patent applications 31,685-000 and 31,686-000.
27. Grau, D. R., et al., Ophtalmol. Vis. Sci. 30:2474–2480 (1989).
28. Chou, T. C. and Talalay, P., Avv. Enz. Regul. 22:27–55 (1984).
29. Kretsmer, P. J., et al., Growth Factors 5:99–114 (1991).
30. Moscattelli, D., J. Cell. Physiol. 131:123–130 (1987).
31. Ruta, M., et al., Oncogene 3:9–15 (1988).
32. Coughlin, S. R., et al., J. BIOl. Chem. 2563:928–933 (1988).
33. Kornbluth, S., et al., Mol. Cell. Biol. 8:5541–5544 (1988).
34. Lee, P. L., et al., Science 245:57–60 (1989).
35. Pasquale, E. B., and Singer, S. J., Proc. Natl. Acad. Sci. USA 86:5449–5453 (1989).
36. Safran, A., et al., Oncogene 5:635–643 (1990).
37. Rybak, M. E., et al., Blood, 73:1534–1539 (1989).
38. Maniatis et al., *Molecular Cloning. A laboratory Manual.* Cold Spring Harbor Laboratory, 1982.
39. Kamholz, P.N.A.S. USA 83:54962–54966 (1986).
40. Sanger, et al., P.N.A.S. USA 74:5463–5467 (1988).
41. Laemmli, Nature, 227:680–685 (1970).
42. Rauvala, EMBO J. 8:2933–2941 (1989).
43. Milner et al., Biochem. Biophys. Res. Comm. 154: 1096–1103 (1989).
44. Von Heijne, J. Mol. Bio. 184: 99–105 (1985).
45. Studier, et al., Meth. Enzymol. 185: 60–69 (1990).
46. Gautschi-Sova et al., Biochem. Biophys, Res. Comm. 140: 1874–1880 (1986).
47. Aviv and Leder, P.N.A.S. U.S.A. 69: 1408–1412 (1972).
48. Kamholz, P.N.A.S. U.S.A. 83: 4962–4966 (1986).
49. Sanger, et al., P.N.A.S. U.S.A. 74: 5463–5467 (1988).
50. Laemmli, Nature 227: 680–685 (1970).
51. von Heijne, Nucl. Acids. Res. 14: 4683–4690 (1986).

What is claimed is:

1. A method of inhibiting the infectivity of a Herpesviridae virus which comprises contacting the virus or a cell susceptible to infection by said virus with an effective amount of a pharmaceutical composition containing HBNF, MK or a combination thereof in a sufficient amount to inhibit the infectivity of the virus.

2. The method according to claim 1, wherein the Herpesviridae virus is selected from the group consisting of an α-herpes virus and a β-herpes virus.

3. The method according to claim 2, wherein the herpes virus is selected from the group consisting of herpes simplex, a virus causing genital herpes, varicella zoster virus and cytomegalovirus.

4. A method of treating a Herpesviridae viral infection in a subject which comprises administering to the subject an effective amount of a pharmaceutical composition containing HBNF, MK or a combination thereof in a sufficient amount to treat the viral infection in the subject.

5. The method according to claim 4, wherein the treatment is prophylactic.

6. The method according to claim 4, wherein the Herpesviridae virus is selected from the group consisting of an α-herpes virus and a β-herpes virus.

7. The method according to claim 6, wherein the herpes virus is selected from the group consisting of herpes simplex, a virus causing genital herpes, varicella zoster virus and cytomegalovirus.

* * * * *